United States Patent

Hsu

[11] Patent Number: 5,411,933
[45] Date of Patent: May 2, 1995

[54] BROMOPROPARGYL QUARTERNARY AMMONIUM COMPOUNDS HAVING ANTIMICROBIAL ACTIVITY

[75] Inventor: Adam C. Hsu, Lansdale, Pa.

[73] Assignee: Rohm & Haas Company, Philadelphia, Pa.

[21] Appl. No.: 209,853

[22] Filed: Mar. 11, 1994

[51] Int. Cl.[6] .................. C07C 211/63; C07C 305/08; C07D 265/28; C07D 207/09
[52] U.S. Cl. .................... 504/156; 504/155; 504/158; 504/224; 504/248; 504/283; 504/345; 514/231.2; 514/315; 514/408; 514/642; 544/106; 544/129; 548/400; 558/27; 562/84; 562/114; 562/493; 562/584
[58] Field of Search .......... 564/291; 558/27; 548/400; 504/155, 156, 158, 224, 248, 283, 345; 514/231.2, 315, 408, 642; 544/106, 129; 562/84, 114, 493, 584, 607

[56] References Cited

U.S. PATENT DOCUMENTS

| | | | |
|---|---|---|---|
| 3,923,870 | 12/1975 | Singer | 260/482 |
| 4,442,122 | 4/1984 | Engelhart et al. | 504/158 |
| 4,521,412 | 6/1985 | Schmitt et al. | 564/291 |
| 5,102,898 | 4/1992 | Hsu | 514/375 |
| 5,156,665 | 10/1992 | Sherba et al. | 504/156 |
| 5,209,930 | 5/1993 | Bowers-Daines et al. | 424/401 |

FOREIGN PATENT DOCUMENTS 365121 4/1990 European Pat. Off. .
539114 4/1993 European Pat. Off. .
6354306 3/1988 Japan .

Primary Examiner—Joseph E. Evans
Attorney, Agent, or Firm—Michael B. Fein

[57] ABSTRACT

Antimicrobial compounds of the formula

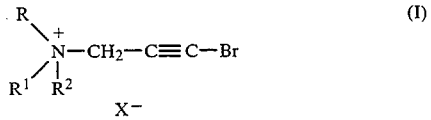

wherein
R, $R^1$ and $R^2$ are selected according to the following:
  A. R is ($C_{11}$–$C_{16}$) alkyl (straight or branched), and $R^1$ and $R^2$ are joined to form a morpholine, pyrrolidine, or piperidine ring with the N;
  B. R is ($C_{11}$–$C_{16}$) and $R^1$ and $R^2$ are independently selected from ($C_1$–$C_3$) alkyl which in the case of $C_3$ can be branched; and
  C. $R^1$ and $R^2$ are the same and are ($C_6$–$C_{12}$) alkyl, straight or branched, and R is ($C_1$–$C_{16}$) alkyl, straight or branched; and
$X^-$ = an anion preferably selected from chlorine, bromine, iodine, phosphate, acetate, benzoate, citrate, tartrate, alkyl- or aryl-sulfonate, and alkylsulfate.

10 Claims, No Drawings

BROMOPROPARGYL QUARTERNARY AMMONIUM COMPOUNDS HAVING ANTIMICROBIAL ACTIVITY

BACKGROUND OF THE INVENTION

This invention relates to novel compounds having antimicrobial activity, their use and compositions comprising such compounds.

DESCRIPTION OF THE PRIOR ART

Certain iodopropargyl compounds have been recognized as having antimicrobial activity. See, for example, U.S. Pat Nos. 3,923,870, 5,209,930 and 4,521,412, European Patent Application 0,365,121 and Japanese Patent Application 63/054,306. None of the aforementioned references teach or suggest bromopropargyl analogs. U.S. Pat. No. 5,102,898 discloses both iodopropargyl and bromopropargyl benzoxazolones having microbicidal activity, but the only two bromopropargyl compounds disclosed therein were much less active than their corresponding iodopropargyl compounds.

Iodopropargyl quaternary ammonium salts have been taught in U.S. Pat. No. 4,521,412 and European Patent Application 539,114-A, but in neither case were bromopropargyl analogs suggested. Although bromopropargyl analogs would have been expected to be much less expensive to synthesize, it was also expected that the bromopropargyl analogs would have been much less active as microbicides.

SUMMARY OF THE INVENTION

It is an object of the present invention to provide novel antimicrobial compounds which are less expensive and yet as effective as their corresponding compounds of the prior art. It is another object of the present invention to provide compositions comprising such compounds and a process for using such compounds. These objects and others which will become apparent from the following disclosure are achieved by the present invention which comprises in one aspect compounds having antimicrobial activity having the formula:

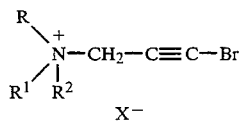

wherein
R, $R^1$ and $R^2$ are selected according to the following:
A. R is ($C_{11}$–$C_{16}$) alkyl (straight or branched), and $R^1$ and $R^2$ are joined to form a morpholine, pyrrolidine, or piperidine ring with the N;
B. R is ($C_1$–$C_{16}$) and $R^1$ and $R^2$ are independently selected from ($C_1$–$C_3$) alkyl which in the case of $C_3$ can be branched; and
C. $R^1$ and $R^2$ are the same and are ($C_6$–$C_{12}$) alkyl, straight or branched, and R is ($C_1$–$C_{16}$) alkyl, straight or branched; and
X=an anion, preferably selected from chlorine, bromine, iodine, phosphate, acetate, benzoate, citrate, tartrate, alkyl- or aryl-sulfonate, alkylsulfate.

In another aspect, the invention comprises the use of such compounds to control microbes and compositions comprising such compounds which are useful in the field of antimicrobial compositions.

As used herein, the term antimicrobial refers to the elimination of or the inhibition of growth of microbial organisms such as bacteria, algae, yeasts, fungi and viruses.

DETAILED DESCRIPTION OF THE INVENTION AND THE PREFERRED EMBODIMENTS

In view of the fact that compounds comprising a bromopropargyl group were either not suggested in the patent literature relating to iodopropargyl analogs or were taught to have significantly less activity, there was a prejudice in the prior art against the synthesis and use of such bromopropargyl analogs. The patent literature pertaining to iodopropargyl quaternary ammonium compounds did not even mention the bromopropargyl analogs. Therefore, it was very surprising that some of the bromopropargyl analogs had much better activity than their corresponding iodopropargyl analogs, and that some had relatively equal activity.

Compounds of formula I may be prepared, for example, by the reaction of a tertiary amine of formula (III) with a bromopropargyl intermediate of formula (IV), in the presence of a solvent at a temperature between 20° to 100° C. and reaction time being preferably at least one hour:

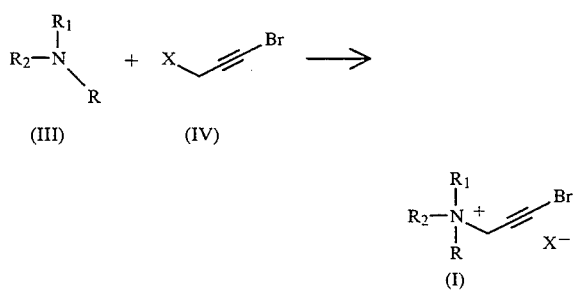

Examples of compounds of formula (III) are N-tetradecyl pyrrolidine, N-tetradecyl piperidine, N-tetradecyl morpholine, trioctylamine, dimethyl dodecyl amine, etc. These tertiary amines are either commercially available or can be prepared by following the method in literature.

Examples for formula (IV) are bromopropargyl benzenesulfonate, bromopropargyl methanesulfonate, bromopropargyl bromide, and bromopropargyl iodide.

Examples of solvents are acetone, methylene chloride, water, alcohol, acetonitrile, ether, and tetrahydrofuran.

Compounds of formula (IV) may be prepared, for example, by the reaction of bromopropargyl alcohol with sulfonyl chloride (VI) to form a bromopropargyl alkyl or aryl sulfonate (V), which is a species of the generic formula (IV), as depicted below, wherein $R^3$ may be alkyl ($C_1$–$C_{16}$); phenyl; or phenyl substituted with Cl, Br, $NO_2$, CN, or lower alkyl:

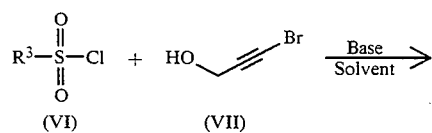

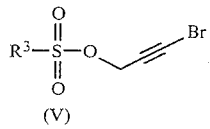

(V)

When X is Br in a compound of the formula (IV), such compound can be prepared by the reaction of (V) with NaBr or KBr in acetone as depicted as below wherein (VIII) is a species of the generic formula (IV):

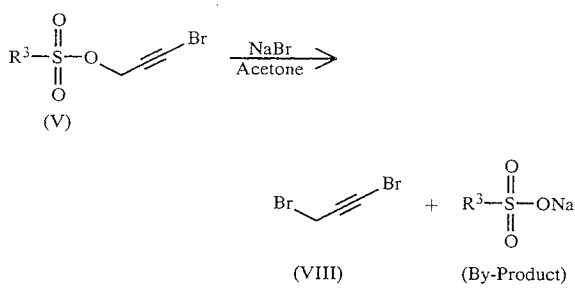

The needed bromopropargyl alcohol may be prepared by reacting propargyl alcohol with NaBr in the presence of a base (e.g. NaOH) and an oxidant (e.g. NaOCl) in water at the temperature between 0° to 25° C.

The following examples set forth a few embodiments of the invention. All parts and percentages are be weight unless otherwise indicated.

EXAMPLES

1. Preparation of Bromopropargyl Alcohol (VII)

To a solution of 28 g (0.5 mole) propargyl alcohol in 200 mL water were added subsequently solid NaOH (30 g, 0.75 mole) and 51.5 g (0.5 mole) NaBr. The mixture was cooled to 0° to −10° C. and one equivalent of 5.35% NaOCl solution was added dropwise over a 3 hour period. The reaction mixture was stirred at 0°–5° C. for 6 hrs. While the solution was still cool, it was acidified with conc. HCl. The mixture is extracted 5 times with methylene chloride and washed with water, dilute NaHSO$_3$ solution, water and brine, and then dried over magnesium sulfate, filtered, and concentrated to give bromopropargyl alcohol (VII).

2. Synthesis of Bromopropargyl p-Toluenesulfonate

In a 100 mL 3-necked round bottom flask, equipped with a magnetic stirrer, nitrogen inlet, thermometer, addition funnel, and ice bath, were placed bromopropargyl alcohol (5 g, 0.037 mole) and tetrahydrofuran (10 mL). A cold solution of NaOH (2.2 g, 0.55 mole) in water (10 mL) was added. To the above stirred mixture a solution of p-toluenesufonyl chloride (7.06 g, 0.037 mole) in tetrahydrofuran (10 mL) was slowly added. The reaction mixture was stirred at 0°–5° C. for 4 hrs. The reaction mixture was then poured into ice water and the resultant white precipitate was collected by suction-filtration and washed with water. After drying in air, an off-white solid was obtained yielding 9.9 g (92.5% yield) m.p. =43°–46° C. An NMR (CDCl$_3$) spectrum indicated the desired compound (V, R$^3$=p-tolyl). This compound is used in the next example without further purification.

3. Synthesis of 4-Bromopropargyl-4-tetradecyl-morpholinium p-toluenesulfonate (Compound 31).

To a stirred solution of 4-tetradecyl morpholine (1.5 g, 0.0053 mole) in acetone (10 mL) at room temperature was added bromopropargyl p-toluenesulfonate (1.5 g, 0.0053 mole). The mixture was stirred at room temperature for 3 days. Hexane (50 mL) was added and the resultant white precipitate was collected by suction-filtration and washed with hexane affording 1.8 g (60% yield) of a white solid. m.p. =134°–136° C. An NMR spectrum showed the desired compound. An elemental analysis provided the following:

|  | % C | % H | % N | % Br | % S |
| --- | --- | --- | --- | --- | --- |
| Calculated | 58.73 | 8.10 | 2.45 | 13.95 | 5.60 |
| Found | 59.65 | 8.52 | 2.47 | 12.88 | 5.60 |

4. Synthesis of tri-n-octyl-bromopropargyl ammonium benzenesulfonate (Compound 18)

To a 100 mL round-bottomed flask, equipped with a magnetic stirrer, were added trioctylamine (2.57 g, 0.007 mole), bromopropargyl benzenesulfonate (1.93 g, 0.007 mole), and dry acetone (10 mL). The reaction mixture was stirred at room temperature for 18 hrs. Ether was then added yielding a tar. A pure product was obtained by column chromatography eluting with ether/aqueous acetone affording a solid, 1.95 g (yield =52% ), mp=51°–54° C. An NMR also showed the desired compound. An elemental analysis provided the following:

|  | % C | % H | % N | % Br | % S |
| --- | --- | --- | --- | --- | --- |
| Calculated | 63.04 | 9.30 | 2.23 | 12.71 | 5.10 |
| Found | 63.07 | 9.56 | 2.22 | 10.15 | 5.19 |

5. Preparation of Compounds of the Invention

The following compounds were prepared and designated compounds 1 to 25:

|  | Melting Point (°C.) |
| --- | --- |
| 1. 1-tetradecyl-1-(3-bromopropargyl)-pyrrolidinium 4-methylbenzenesulfonate | 75–80 |
| 2. 1-tetradecyl-1-(3-bromopropargyl)-morpholinium benzenesulfonate | 111–114 |
| 3. 1-tetradecyl-1-(3-bromopropargyl)-morpholinium 4-methylbenzenesulfonate | 134–136 |
| 4. 1-tetradecyl-1-(3-bromopropargyl)-morpholinium methanesulfonate | semi-solid |
| 5. 1-tetradecyl-1-(3-bromopropargyl)-pyrrolidinium benzenesulfonate | 92–98 |
| 6. 1-tetradecyl-1-(3-bromopropargyl)-piperidinium methanesulfonate | semi |
| 7. 1-tetradecyl-1-(3-bromopropargyl)-morpholinium n-butanesulfonate | 102–107 |
| 8. 1-tetradecyl-1-(3-bromopropargyl)-pyrrolidinium n-butanesulfonate | semi |
| 9. 1-tetradecyl-1-(3-bromopropargyl)-morpholinium bromide | oil |
| 10. 1-tridecyl-1-(3-bromopropargyl)-morpholinium bromide | 100–102 |

-continued

| | Melting Point (°C.) |
|---|---|
| 11. 1-hexadecyl-1-(3-bromopropargyl)-morpholinium bromide | 136–138 |
| 12. 1-dodecyl-1-(3-bromopropargyl)-morpholinium 4-methylbenzenesulfonate | 123–127 |
| 13. 1-hexadecyl-1-(3-bromopropargyl)-morpholinium methanesulfonate | 95–98 |
| 14. 1-tetradecyl-1-(3-bromopropargyl)-(2-methyl)piperidinium 4-methylbenzenesulfonate | semi |
| 15. 1-tetradecyl-1-(3-bromopropargyl)-(2-methyl)piperidinium methanesulfonate | semi |
| 16. 1-tetradecyl-1-(3-bromopropargyl)-(2-methyl)piperidinium benzenesulfonate | semi |
| 17. 1-tetradecyl-1-(3-bromopropargyl)-piperidinium benzenesulfonate | 130–132 |
| 18. trioctyl-(3-bromopropargyl) ammonium benzenesulfonate | 51–54 |
| 19. dimethyloctyl(3-bromopropargyl) ammonium benzenesulfonate | 138–141 |
| 20. trioctyl(3-bromopropargyl) ammonium 4-methylbenzenesulfonate | 64–66 |
| 21. dimethyldodecyl ammonium 4-methylbenzenesulfonate | 137–140 |
| 22. trihexyl(3-bromopropargyl) ammonium benzenesulfonate | semi-solid |
| 23. trihexyl(3-bromopropargyl) ammonium 4-methylbenzenesulfonate | semi-solid |
| 24. tridodecyl(3-bromopropargyl) ammonium 4-methylbenzenesulfonate | semi-solid |
| 25. methyldioctyl(3-bromopropargyl) ammonium 4-methylbenzenesulfonate | 103–105° C. |
| 26. methyldioctyl(3-bromopropargyl) ammonium benzenesulfonate | 95–99° C. |
| 27. tri-iso-octyl(3-bromopropargyl) ammonium benzenesulfonate | oil |
| 28. tri-iso-decyl(3-bromopropargyl) ammonium benzenesulfonate | oil |
| 29. tri-n-nonyl (3-bromopropargyl) ammonium benzenesulfonate | — |
| 30. tri-n-decyl (3-bromopropargyl) ammonium benzenesulfonate | — |
| 31. Comparative-iodopropargyl analogue of compound 22. | |
| 32. Comparative-iodopropargyl analogue of compound 3. | |
| 33. Comparative-iodopropargyl analogue of compound 17. | |
| 34. Comparative-iodopropargyl analogue of compound 18. | |

6. Biocidal Activity

Bactericidal and fungicidal evaluations of the compounds of Example 5 were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 500, 250, 125, 63, 31, 16, 8 and 4, 2, 1, 0.5, 0.25 ppm respectively.

Each vessel is then inoculated with a cell suspension of the appropriate test organism. Bacteria are grown in broth, fungi or agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The vessels are then incubated at the appropriate temperature. After the incubation, the vessels are examined for growth/no growth. The minimum inhibitory concentration (MIC) is defined as the lowest concentration of compounds that results in complete inhibition of growth of the test organism.

The organisms tested to demonstrate biocidal activity are shown in the following table.

TABLE 1

Microorganisms used in the Biocides Tests

| Name | Gram | ATCC | Abbreviations Used |
|---|---|---|---|
| BACTERIA | | | |
| 1. *Pseudomonas aeruginosa* | (−) | 15442 | Psae |
| 2. *Escherichia coli* | (−) | 11229 | Ecol |
| FUNGUS | | | |
| 3. *Aspergillus niger* | | 6275 | Anig |
| 4. *Rhodotorula rubra* | | | Rrub |

The results of minimum inhibitory concentration (MIC) tests of compounds of this invention are shown in Table 2.

TABLE 2

Biocidal MIC Results

| Compound No. | MIC (TSB media) | | | |
|---|---|---|---|---|
| | Ecol | Psae | Anig | Rrub |
| 1 | 8 | >500 | <4 | <4 |
| 2 | 8 | 63 | <4 | <4 |
| 3 | 8 | 250 | <4 | <4 |
| 4 | 32 | 500 | <4 | <4 |
| 5 | 8 | 500 | <4 | <4 |
| 6 | >500 | >500 | <4 | <4 |
| 7 | 16 | 500 | <4 | <4 |
| 8 | <4 | 250 | <4 | <4 |
| 9 | 8 | 125 | <4 | <4 |
| 10 | 32 | 250 | 16 | <4 |
| 11 | 16 | 500 | <4 | <4 |
| 12 | 63 | 500 | 16 | <4 |
| 13 | >500 | 500 | 16 | 32 |
| 14 | <4 | 125 | <4 | <4 |
| 15 | 5 | 300 | 3.2 | <1 |
| 16 | 8 | 500 | <4 | <4 |
| 17 | <4 | 32 | <4 | <4 |
| 18 | <4 | 16 | 1.6 | 1.6 |
| 19 | 16 | 250 | <4 | <4 |
| 20 | <4 | 8 | 3.2 | 0.8 |
| 21 | 32 | 250 | 6.3 | 3.2 |
| 22 | 125 | 500 | 25 | 12.5 |
| 23 | 250 | 500 | 50 | <50 |
| 24 | 500 | 500 | >50 | >50 |
| 25 | 32 | 500 | 12.5 | 6.3 |
| 26 | 32 | 500 | 12.5 | 6.3 |
| 27 | — | — | — | — |

TABLE 2-continued

| Compound No. | Biocidal MIC Results MIC (TSB media) | | | |
|---|---|---|---|---|
| | Ecol | Psae | Anig | Rrub |
| 28 | — | — | — | — |
| 29 | — | — | — | — |
| 30 | — | — | — | — |
| 31 (comp.) | 63 | >500 | 12.5 | 6.3 |
| 32 (comp.) | 8 | 125 | 4 | 4 |
| 33 (comp.) | 4 | 125 | 4 | 2 |
| 34 (comp.) | >500 | 1.6 | 1.6 | 1.6 |

I claim:

1. Compounds having antimicrobial activity having the formula:

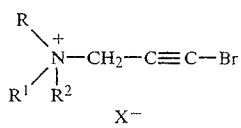

wherein
R, $R^1$ and $R^2$ are selected according to the following:
- A. R is ($C_{11}$–$C_{16}$) alkyl (straight or branched), and $R^1$ and $R^2$ are joined to form a morpholine, pyrrolidine, or piperidine ring with the N;
- B. R is ($C_{11}$–$C_{16}$) and $R^1$ and $R^2$ are independently selected from ($C_1$–$C_3$) alkyl which in the case of $C_3$ can be branched; and
- C. $R^1$ and $R^2$ are the same and are ($C_6$–$C_{12}$) alkyl, straight or branched, and R is ($C_1$–$C_{16}$) alkyl, straight or branched; and
$X^-$ = an anion.

2. Compound according to claim 1 wherein $X^-$ is an anion selected from the group consisting of chlorine, bromine, iodine, phosphate, acetate, benzoate, citrate, tartrate, alkyl-sulfonate or aryl-sulfonate, and alkylsulfate.

3. Compound according to claim 1 wherein X is selected from the group consisting of benzene sulfonate and methane sulfonate.

4. Compound according to claim 1 selected from the group consisting of 1-tetradecyl-1-(3-bromopropargyl)-pyrrolidinium 4-methylbenzenesulfonate; 1-tetradecyl-1-(3-bromopropargyl)-morpholinium benzenesulfonate; 1-tetradecyl-1-(3-bromopropargyl)-morpholinium 4-methylbenzenesulfonate; 1-tetradecyl-1-(3-bromopropargyl)-morpholinium methanesulfonate; 1-tetradecyl-1-(3-bromopropargyl)pyrrolidinium benzenesulfonate; 1-tetradecyl-1-(3-bromopropargyl)-piperidinium methanesulfonate; 1-tetradecyl-1-(3-bromopropargyl)-morpholinium n-butanesulfonate; 1-tetradecyl-1-(3-bromopropargyl)-pyrrolidinium n-butanesulfonate; 1-tetradecyl-1-(3-bromopropargyl)-morpholinium bromide; 1-tridecyl-1-(3-bromopropargyl)morpholinium bromide; 1-hexadecyl-1-(3-bromopropargyl)-morpholinium bromide; 1-dodecyl-1-(3-bromopropargyl)-morpholinium 4-methylbenzenesulfonate; 1-hexadecyl-1-(3-bromopropargyl)-morpholinium methanesulfonate; 1-tetradecyl-1-(3-bromopropargyl)-(2-methyl)-piperidinium 4-methylbenzenesulfonate; 1-tetradecyl-1-(3-bromopropargyl)-(2-methyl)piperidinium methanesulfonate; 1-tetradecyl-1-(3-bromopropargyl-(2-methyl)piperidinium benzenesulfonate; 1-tetradecyl-1-(3-bromopropargyl)-piperidinium benzenesulfonate; trioctyl-(3-bromopropargyl) ammonium benzenesulfonate; dimethyloctyl(3-bromopropargyl) ammonium benzenesulfonate; trioctyl(3-bromopropargyl) ammonium 4-methylbenzenesulfonate; dimethyldodecyl ammonium 4-methylbenzenesulfonate; trihexyl(3-bromopropargyl) ammonium benzenesulfonate; trihexyl(3-bromopropargyl) ammonium 4-methylbenzenesulfonate; tridodecyl(3-bromopropargyl) ammonium 4-methylbenzenesulfonate; methyldioctyl(3-bromopropargyl) ammonium 4-methylbenzenesulfonate; methyldioctyl(3-bromopropargyl) ammonium benzenesulfonate; tri-iso-octyl(3-bromopropargyl) ammonium benzenesulfonate; and tri-iso-decyl (3-bromopropargyl) ammonium benzenesulfonate.

5. Compound according to claim 1 wherein R, $R^1$, and $R^2$ are each n-octyl.

6. Process of inhibiting the growth of microbial organisms comprising introducing a microbicidally effective amount of one or more compounds according to claim 1 onto, into, or at a locus subject to microbial attack to control microbial growth.

7. Process according to claim 6 wherein said microbial organism which is being controlled is selected from the group consisting of bacteria, fungi, yeasts, algae, and viruses.

8. The process according to claim 6 wherein said locus is selected from the group consisting of wood, paint, adhesive, glue, paper, pulp/paper slurries, textile, leather, plastics, cardboard, lubricants, cosmetics, food, caulking, feed, and industrial cooling water.

9. The process of claim 6 wherein the amount of said compound is about 5 to about 1000 ppm based on weight of said locus.

10. A composition useful as a microbicide comprising an effective amount of a compound according to claim 1 and a carrier.

* * * * *